(12) United States Patent
Reinhardt et al.

(10) Patent No.: US 9,012,630 B2
(45) Date of Patent: Apr. 21, 2015

(54) METHOD FOR PRODUCING BRIDGED MANGANESE COMPLEXES OF TRIAZACYCLONONANE

(75) Inventors: Gerd Reinhardt, Kelkheim (DE);
Michael Best, Bad Soden (DE);
Christian Sidot, Compiegne (FR)

(73) Assignee: Clariant International Ltd., Muttenz (CH)

( * ) Notice: Subject to any disclaimer, the term of this patent is extended or adjusted under 35 U.S.C. 154(b) by 527 days.

(21) Appl. No.: 13/394,968

(22) PCT Filed: Sep. 10, 2010

(86) PCT No.: PCT/EP2010/005569
§ 371 (c)(1),
(2), (4) Date: Apr. 13, 2012

(87) PCT Pub. No.: WO2011/032666
PCT Pub. Date: Mar. 24, 2011

(65) Prior Publication Data
US 2012/0202990 A1   Aug. 9, 2012

(30) Foreign Application Priority Data
Sep. 18, 2009 (EP) .................................... 09290713

(51) Int. Cl.
*C07F 13/00* (2006.01)
*B01J 31/18* (2006.01)
*B01J 31/22* (2006.01)

(52) U.S. Cl.
CPC ............ *C07F 13/005* (2013.01); *B01J 31/182* (2013.01); *B01J 31/2208* (2013.01); *B01J 2531/0216* (2013.01)

(58) Field of Classification Search
None
See application file for complete search history.

(56) References Cited

U.S. PATENT DOCUMENTS

| 5,516,738 A | 5/1996 | Jureller et al. |
| 2001/0025695 A1 | 10/2001 | Patt et al. |
| 2001/0044402 A1 | 11/2001 | Dal et al. |
| 2002/0066542 A1 | 6/2002 | Jakob et al. |
| 2004/0138506 A1 | 7/2004 | Suess-Fink et al. |
| 2009/0126121 A1 | 5/2009 | de Almeida et al. |

FOREIGN PATENT DOCUMENTS

| EP | 0458397 A2 | 11/1991 |
| EP | 0458398 A2 | 11/1991 |
| EP | 0530870 A1 | 3/1993 |
| WO | 9325562 A1 | 12/1993 |
| WO | 9606154 A1 | 2/1996 |
| WO | 02088063 A1 | 11/2002 |
| WO | 2008086937 A2 | 7/2008 |

OTHER PUBLICATIONS

Koek. Journal of the Chemical Society, Dalton Transactions, 1996, 353-62.*

* cited by examiner

*Primary Examiner* — Noble Jarrell
(74) *Attorney, Agent, or Firm* — Michael W. Ferrell

(57) ABSTRACT

The invention relates to a method for producing manganese complex compounds of the general formula (1), wherein M, X, L, z, Y and q are defined as in claim 1. The method is characterized by the following steps: a) reacting one or more bivalent metal salts with the ligand L in water as the solvent to form a coordination compound from the one or more bivalent metal salt and the ligand L, the one or more bivalent metal salts being selected from bivalent manganese salts and iron salts and at least one bivalent metal salt being a bivalent manganese salt, b) oxidizing the coordination compound of step a) with an oxidant while at the same time maintaining a pH of 11 to 14, to transform the metal M from the bivalent to the trivalent and/or tetravalent form, c) reducing the pH of the reaction mixture to a pH of 4 to 9 and removing any metal oxides or metal hydroxides of the metal M formed and d) adding, at a pH of 4 to 9, a salt of the formula $Me_zY_q$, wherein Me represents an alkali metal ion, ammonium ion or an alkanol ammonium ion, and Y, z and q are defined as in formula (1).

$$[LM\overset{X}{\underset{X}{\overset{\displaystyle\diagup}{\diagdown}}}\!\!\overset{\displaystyle\diagdown}{\underset{\displaystyle\diagup}{X}}ML]^z\ Y_q \qquad (1)$$

19 Claims, No Drawings

METHOD FOR PRODUCING BRIDGED MANGANESE COMPLEXES OF TRIAZACYCLONONANE

The invention relates to a method for producing sparingly soluble, crystalline metal complex compounds which are used as bleach catalysts in detergents and cleaners.

In European powder detergents, the bleach component has for a long time been based on bleaches which release peroxide compounds during washing. These highly oxidative compounds very effectively remove a very wide variety of stain types, such as, for example, from tea, wine and fruits, without impacting on the environment, as is the case with the chlorine bleaches that are widespread in other countries. Depending on the peroxide compound used, mostly perborates or percarbonates, the washing temperatures required for effective bleaching are between 60 and 95° C. At temperatures below 60° C., by contrast, the effectiveness of the oxygen bleaches drops considerably. For economic and ecological reasons, endeavors are therefore made to find compounds which permit an oxygen bleaching even at low temperatures. Whereas for the purposes of improving the bleaching performance of detergents on textile fabrics at low temperatures, mostly bleach activators such as tetraacetylethylenediamine (TAED), nonanoyloxybenzenesulfonate-sodium (NOBS) or decanoyloxybenzoic acid (DOBA) have caught on, for the purposes of cleaning hard surfaces, e.g. in dishwashing detergents, bleach catalysts are increasingly being used alongside bleach activators. Here, a good cleaning performance on stubborn tea stains in particular is expected. More recently, bleach catalysts have also been used to a greater extent in textile and paper bleaching and also in chemical synthesis (oxidation reactions).

These bleach catalysts are mostly metal-containing compounds of iron, cobalt or manganese. On the one hand, relatively simple compounds such as metal salts (e.g. manganese acetates) or coordination compounds such as cobalt pentamineacetates are used, on the other hand transition metal complexes with open-chain or cyclic ligands are of particular interest since they surpass the bleaching performance of the simple systems many times over. From the series of the last-mentioned catalysts, in particular manganese or iron complexes comprising ligands based on triazacyclononane and derivatives thereof have particular bleaching-active effectiveness or high oxidation power.

Examples of production and use of such metal complexes are described inter alia in US 2009/0126121, WO 2008/086937, US 2002/0066542, US 2001/0044402, US 2001/0025695, U.S. Pat. No. 5,516,738, WO 2000/088063 and EP 0 530 870. For their simple handling during production, processing and use, it is in many cases necessary to use solid, low hygroscopicity compounds. Here, bleach catalysts and oxidation catalysts which comprise large-volume counterions such as hexafluorophosphate, perchlorate or tetraphenylborate in particular have proven useful. Such complexes are described e.g. in EP 0 458 397, EP 0 458 398 and WO 96/06154.

A series of production methods is known for the synthesis of such transition metal complexes of triazacyclononane and derivatives thereof. Thus, e.g. WO-A-93/25562 describes a method for producing effective manganese complex catalysts which comprises the following steps:
i) reaction of a manganese(II) salt with a triazacyclononane derivative such as 1,4,7-trimethyl-1,4,7-triazacyclononane in the presence of a counterion salt such as $KPF_6$ in an aqueous-alcoholic medium to form a manganese coordination compound,
ii) and subsequent oxidation of the manganese coordination compound with an oxidizing agent, where at the same time a pH of at least 12 is maintained, to form the desired manganese complex, where the manganese is preferably present in oxidation state +3 and/or +4,
iii) the reaction mixture obtained in step ii) is adjusted to a pH from 7 to 9, then the manganese oxides formed are filtered off and the manganese complex is isolated by evaporating the solvent mixture. The yields attained are 59 to 73%.

In a similar way, in WO 96/06145, an ethyl-bridged triazacyclononane ligand is complexed with manganese(II) acetate in the presence of $KPF_6$ and then converted to the desired manganese(III/IV) complex by oxidation with hydrogen peroxide.

In EP 0 522 817, processing is in a nonaqueous solvent (acetonitrile), where a manganese(III) salt is in turn converted in the presence of the ligand and the counterion to the manganese(III) complex, which is then oxidized to the manganese (IV) complex.

As well as at times low yields, the described methods also throw up problems with regard to implementation on an industrial scale:
The solvent mixture water/alcohol (ethanol) is used in large amounts in order to achieve solubility of the manganese complex. This results in low space-time yields (0.05 kg/l), and moreover large amounts of solvent have to be evaporated in order to isolate the complex.
During the thermal removal of the large amounts of solvent for the purposes of isolating the pulverulent manganese complex, on an industrial scale, the target product partially decomposes with the formation of manganese oxide, which has to be separated off. However, a recrystallization constitutes an additional reaction step.
The manganese complex is often contaminated with an undesired by-product. This is the salt formed from the ligand (triazacyclononane (derivative)) and the counterion (e.g. $PF_6$). Its removal requires a further purification step.

There was therefore a need for a new method, which can be carried out industrially, for producing sparingly soluble, crystalline metal complexes, preferably manganese complexes, which can optionally comprise iron as a further metal, which leads to an improved space-time yield and makes do with a small number of purification steps.

Surprisingly, it has now been found that this object is achieved and the production of said metal complexes is also possible when the starting solutions are relatively concentrated and this concentration of solids is essentially retained until the end of the reactions. In this method, water is used as the sole solvent.

In a first reaction step, firstly an organic ligand such as, for example, the triclononane ligand is reacted with a metal salt such as e.g. manganese salt, the counterion required later not being present. The metal ion of the complex formed is oxidized at increased pH to give the desired oxidation state, then the metal oxides, such as e.g. manganese oxides, formed as by-product are filtered off, and only then is the sparingly soluble complex precipitated out and isolated by adding the counterion.

With the present invention, a gentle method for producing metal complexes is provided which makes do without organic solvent, can be converted to an industrial scale and produces high-purity products in high space-time yield and purity. In particular, the product is free from by-products such as manganese oxides and ligand salts, meaning that it is possible to dispense with a further purification step after the synthesis.

The present invention provides a method for producing manganese complex compounds of the formula (1)

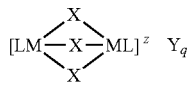

(1)

in which
M is selected from manganese and iron in oxidation state III or IV, but where at least one M is a manganese in oxidation state III or IV,
X independently of the others is a coordinating or bridging species, selected from $H_2O$, $O_2^{2-}$, $O_2^-$, $OH^-$, $HO_2^-$, $SH^-$, $S^{2-}$, $SO$, $Cl^-$, $N^{3-}$, $SCN^-$, $N_3^-$, $RCOO^-$, $NH_2^-$ and $NR_3$, where R is a radical selected from H, alkyl and aryl,
L is an organic ligand which contains at least two nitrogen atoms coordinated to manganese and optionally to iron,
z is an integer from −4 to +4,
Y is a mono- or multivalent counterion from the group hexafluorophosphate, perchlorate or tetraphenylborate, which leads to the charge neutrality of the complex, and
q is an integer from 1 to 4,
which comprises the following steps:
a) reacting one or more divalent metal salts, where the one or more divalent metal salts are selected from divalent manganese and iron salts and at least one divalent metal salt is a divalent manganese salt, with the ligand L in water as solvent for forming a coordination compound of the one or more divalent metal salts and the ligand L,
b) oxidation of the coordination compound from step a) with an oxidizing agent, where at the same time a pH from 11 to 14 and preferably 12 to 14 is maintained, for converting the metal M from the divalent state to the tri- and/or tetravalent state,
c) reducing the pH of the reaction mixture to a pH from 4 to 9, preferably from 5 to 8, and separating off any metal oxides or hydroxides of the metal M formed and
d) addition of a salt of the formula $Me_zY_q$, in which Me is an alkali metal ion, an ammonium ion or an alkanolammonium ion, and Y, z and q have the stated meanings, at a pH from 4 to 9 and preferably from 5 to 8.

The alkyl group specified as radical R is preferably $C_1$ to $C_4$-alkyl and the aryl group specified as radical R is preferably $C_6H_5$ (phenyl).

In a preferred embodiment of the method according to the invention, the crystalline precipitated manganese complex compound of the formula (1) is isolated in a step e), preferably by filtration or centrifugation.

The method according to the invention differs from the prior art in that the reactions can be carried out in concentrated aqueous reaction mixtures and in particular in that the counterion salt $Me_zY_q$ is only introduced into the reaction mixture and reacted after the oxidation step and the removal of the metal oxides and metal hydroxides formed.

In step a) of the method according to the invention, a water-soluble manganese(II) salt and optionally additionally a water-soluble iron(II) salt, preferably from the group of acetates, carbonates, halides, nitrates and sulfates, for example manganese diacetate, manganese dichloride, manganese dibromide, manganese sulfate, manganese dinitrate, iron chloride, iron sulfate or iron nitrate, is reacted with a ligand compound L, preferably in the molar ratio of 4:1 to 1:2, particularly preferably in the molar ratio from 2:1 to 1:1 and especially preferably in the molar ratio from 1.5:1 to 1:1.

Here, the metal(II) salt and the ligand compound are used in a total amount of at least 15 parts by weight per 100 parts by weight of water.

Particularly preferably, all of the M in the formula (1) is manganese in oxidation state III or IV and all of the divalent metal salts from step a) are divalent manganese salts. The divalent metal salt from step a) is especially preferably manganese dichloride 4-hydrate.

The organic ligand L is preferably one which is an at least nine-membered ring in which at least two, preferably three or four, nitrogen atoms are involved in the ring and coordinate with the manganese. Examples which may be mentioned are: 1,4,7-triazacyclononane (TACN), 1,4,7-trimethyl-1,4,7-triazacyclononane (1,4,7-Mea-TACN), 1,5,9-triazacyclododecane (TACD), 1,5,9-trimethyl-1,5,9-triazacyclododecane (1,5,9-Mea-TACD), 1,4,7,10-tetraazacyclododecane (cyclam), 1,4,7,10-tetramethyl-1,4,7,10-tetraazacyclododecane (1,4,7,10-Me₄-cyclam), 2-methyl-1,4,7-trimethyl-1,4,7-triazacyclononane (2-Me-1,4,7-Mea-TACN), 2-methyl-1,4,7-triazacyclononane (2-Me-TACN) or 1,2-bis(4,7-dimethyl-1,4,7-triazacyclon-1-yl)ethane (Me₄-DTNE). From this group, particular preference is given to 1,4,7-trimethyl-1,4,7-triazacyclononane (1,4,7-Mea-TACN) and 1,2-bis(4,7-dimethyl-1,4,7-triazacyclon-1-yl)ethane (Me₄-DTNE). From this group, 1,4,7-trimethyl-1,4,7-triazacyclononane (1,4,7-Mea-TACN) is especially preferred.

According to the invention, the reaction of the manganese (II) salt and optionally additionally of the iron(II) salt with the ligand L in step a) is carried out in water as the sole solvent. Preferably, only enough water is used for the divalent metal salt or the metal(II) salt (i.e. the sum of manganese(II) salt and optionally additionally iron(II) salt) and the ligand compound together to be present in an amount of at least 15 parts by weight per 100 parts by weight of water. The upper limit of the concentration of metal(II) salt and ligand compound can be very high because this and the further reactions can be carried out either in solution or in suspension (dispersion). The upper concentration limit is thus essentially given by the stirrability of the reaction mixtures; the stirrability is also the limiting factor for the space-time yield. The metal(II) salt and the ligand are accordingly used together in an amount of preferably 15 to 55 parts by weight and particularly preferably from 20 to 50 parts by weight, per 100 parts by weight of water. The reaction of the metal(II) salt with the ligand L in water is carried out at a temperature from 10 to 30° C., preferably 15 to 25° C. (room temperature), and atmospheric pressure. Step a) of the method according to the invention leads to the formation of a coordination compound of the metal(II) salt and the ligand compound dissolved in the solvent mixture. When calculating the amount of metal(II) salt and ligand in water, the water of crystallization possibly present in the metal(II) salt is included in the solvent water.

In step b) of the method according to the invention, the metal(II) coordination compound is oxidized at a pH from 11 to 14, preferably from 12 to 13, in the solution obtained in step a), the oxidizing agent and the base for establishing the stated pH preferably being introduced simultaneously. The oxidation is preferably carried out by simultaneously mixing into an oxidizing agent from the group air, pure oxygen, hydrogen peroxide, alkali metal peroxide and alkali metal permanganate and an alkali metal hydroxide into the solution obtained in step a) while maintaining the stated pH. Preferably, the oxidation is carried out by mixing in a (preprepared) mixture consisting of a 0.5 to 35% strength by weight, preferably 3 to 20% strength by weight, aqueous hydrogen peroxide solution and a 5 to 40% strength by weight, preferably 10 to 30% strength by weight, aqueous alkali metal (sodium or potassium) hydroxide solution. As far as the temperature and the pressure are concerned, the oxidation is generally carried out at 3 to 20° C., preferably 5 to 15° C., and atmospheric pressure. Here, the divalent metal used is oxidized to the trivalent or to the preferred tri- and/or tetravalent state.

In step c) of the method according to the invention, the reaction mixture obtained in step b) is adjusted to pH 4 to 9, preferably 5 to 8, by adding an acid such as hydrochloric acid or sulfuric acid, and then metal oxides and metal hydroxides formed in the oxidation step are separated off by customary methods, such as filtration or centrifugation.

In step d), finally, the counterion salt $Me_zY_q$, in which Me is an alkali metal ion, ammonium ion or an alkanolammonium ion, and z, q and Y have the stated meanings, is added to the reaction mixture obtained in step c), and the metal complex as per formula (1) is formed.

The counterion salt $Me_zY_q$ is preferably used in an amount such that the molar ratio of metal(II) salt to $Me_zY_q$ salt used in step a) is 4:1 to 1:4, particularly preferably 2:1 to 1:2 and especially preferably 1:1 to 1:2. Suitable counterion salts are, for example, perchlorates, tetraphenylborates and hexafluorophosphates, with hexafluorophosphates being preferred.

The salt $Me_zY_q$ for introducing the charge-balancing counterion Y (cf. formula (1)) is introduced into the reaction mixture obtained in step c) either in solid form or in water-dissolved form. In a preferred embodiment of the invention, a saturated solution of the salt $Me_zY_q$ is generally added at a temperature of from 5 to 100° C., preferably 40 to 80° C., and atmospheric pressure to the reaction mixture, held at 10 to 40° C. After cooling, the desired metal complex precipitates out as crystalline solid and can be separated off e.g. by filtration or via a centrifuge.

Using the method according to the invention, the dinuclear manganese complex compounds of the formula (1) with preferably tetravalent metal are produced in a gentle manner. Particularly preferred complexes which can be synthesized in this way are:

[Mn$^{(IV)}_2$(μ-O)$_3$(1,4,7-Me$_3$-TACN)$_2$]2PF$_6$*H$_2$O

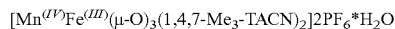
[Mn$^{(IV)}$Fe$^{(III)}$(μ-O)$_3$(1,4,7-Me$_3$-TACN)$_2$]2PF$_6$*H$_2$O

[Mn$^{(IV)}_2$(μ-O)$_3$(1,4,7-Me$_3$-TACN)$_2$]2BF$_4$*H$_2$O

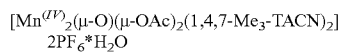
[Mn$^{(IV)}_2$(μ-O)(μ-OAc)$_2$(1,4,7-Me$_3$-TACN)$_2$] 2PF$_6$*H$_2$O

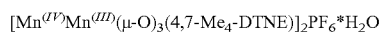
[Mn$^{(IV)}$Mn$^{(III)}$(μ-O)$_3$(4,7-Me$_4$-DTNE)]$_2$PF$_6$*H$_2$O

With the method according to the invention, tri-μ-oxobis [(1,4,7-trimethyl-1,4,7-triazacyclononane)manganese(IV)] bishexafluorophosphate monohydrate can be especially preferably produced.

On account of the relatively small amount of water as the sole solvent and the specific order of the reaction steps, a high space-time yield (about 0.2 kg/l) and a high-purity product are simultaneously achieved. The yields are generally above 80% and the purity is at least 98.5%. The fraction of metal oxides and metal hydroxides, such as e.g. MnO$_2$, is below 0.3% by weight. The metal complex is free from ligand salt (for example salt from the monoprotonated cycloamine and PF$_6$ anion), the formation of which often occurs in the case of the prior art methods (see comparative example below).

A high economic feasibility is achieved because the reactions can be carried out with a small amount of solvent, i.e. in concentrated form, and no distillation costs arise. This has the further advantage that no thermal stressing of the complex takes place.

The metal complexes produced by the method according to the invention are used as oxidation catalysts particularly as bleach component in detergents and cleaners in the home or in institutional laundries, and also in the bleaching of textiles and paper, and also in industrial oxidation reactions.

The invention is illustrated below by reference to examples, although these are in no way to be regarded as a limitation.

COMPARATIVE EXAMPLE 1

In Accordance with WO-A-93/25562 with Alcoholic Solvent and Addition of KPF$_6$ before the Oxidation Step In a 2 liter flask, 28.9 g of manganese dichloride 4-hydrate (0.146 mol) are stirred into a mixture of 530 g of ethanol and 330 g of water and admixed with 25 g of 1,4,7-trimethyl-1,4, 7-triazacyclononane (0.146 mol) and 28.8 g (0.156 mol) of potassium hexafluorophosphate. After the mixture has been stirred for 20 minutes at room temperature, it is cooled to about 5° C. using an ice bath, and a solution of 165 g (0.146 mol) of 3% strength by weight hydrogen peroxide solution and 44 g (0.22 mol) of 20% strength by weight sodium hydroxide solution is added dropwise over 10 minutes. The mixture is then stirred for a further 1 hour in the ice bath at about 5° C., the ice bath is removed and the mixture is after-stirred for 1 hour. For the work-up, the reaction mixture is adjusted to a pH of 8 to 9 with 25.8 g of 1N sulfuric acid, the insoluble solids (manganese oxides) are filtered off with suction and the suction filter-cake is rinsed with about 200 g of water until the water which passes through remains colorless. The filtrate is concentrated by evaporation to crystallize the product to about ⅛ of its volume and the crystals formed are filtered off with suction. After the deep-red crystal slurry has been washed again with 20 g of ethanol, it is dried in a vacuum drying cabinet at 50° C. This gives 43.1 g (73% yield, purity: 90 to 96%) of tri-μ-oxobis[(1,4,7-trimethyl-1,4,7-triazacyclononane)manganese(IV)]bishexafluorophosphate monohydrate. By means of HPLC, 4 to 10% by weight of ligand salt (C$_9$H$_{21}$N$_3$H$^+$PF$_6^-$) can also be detected in the product. (HPLC with reversed-phase column and methanol/water as mobile phase, detection by means of UV at 205 mm).

COMPARATIVE EXAMPLE 2

Addition of KPF$_6$ at a High pH 39.6 g of manganese dichloride 4-hydrate (0.2 mol) are introduced as initial charge in 180 g of water in a 1 liter flask and admixed with 34.3 g of 1,4,7-trimethyl-1,4,7-triazacyclononane (0.2 mol). After the mixture has been stirred for 45 minutes at room temperature, it is cooled to 5° C. and admixed with a mixture of 60.3 g (0.301 mol) of 20% strength by weight sodium hydroxide solution and 226.7 g (0.2 mol) of 3% strength by weight hydrogen peroxide solution with temperature control, i.e. during the addition of this alkaline hydrogen peroxide solution, the temperature of the reaction mixture is kept between 10 and 15° C. Then, 39.4 g (0.214 mol) of potassium hexafluorophosphate are added in solid form at a pH>12.5 and then the mixture is after-stirred for a further 2 to 3 hours at room temperature. For the work-up, the reaction mixture (pH>12.5) is adjusted to a pH of 8 to 9 with 9.7 g of 50% strength by weight sulfuric acid and the solids of the reaction mixture are filtered off with suction over a paper filter. For the complete removal of residual amounts of water-soluble, inorganic salts, the suction filter-cake is washed twice with 70 g of ice-water in each case. Drying in a vacuum drying cabinet at 80° C. gives 64 g (79% yield) of tri-μ-oxobis[(1,4,7-trimethyl-1,4,7-triazacyclononane)manganese(IV)]bishexafluorophosphate monohydrate as 96% solid (according to HPLC). No ligand salt (measurement limit <0.1% by weight) can be detected in the product. The content of manganese dioxide in the product is 4% by weight.

EXAMPLE 1

39.6 g of manganese dichloride 4-hydrate (0.2 mol) are introduced as initial charge in 180 g of water in a 1 liter flask and admixed with 34.3 g of 1,4,7-trimethyl-1,4,7-triazacyclononane (0.2 mol). After the mixture had been cooled to 5° C., a mixture of 60.3 g (0.301 mol) of 20% strength by weight sodium hydroxide solution and 226.7 g (0.2 mol) of 3% strength by weight hydrogen peroxide solution is added with temperature control (10 to 15° C.). When the addition is complete, the reaction mixture (pH>12.5) is adjusted to a pH of 6 with 12.1 g of 50% strength by weight sulfuric acid. The deposited brown-black solids are filtered off with suction and the resulting filtrate is admixed at a pH of 6 with 39.4 g (0.214 mol) of ground potassium hexafluorophosphate (<10 μm) in solid form. The solid produced in the reaction mixture is filtered off with suction and washed twice with 70 g of ice-water in each case. Drying in a vacuum drying cabinet at 80° C. gives 65.4 g (81% yield) of tri-μ-oxobis[(1,4,7-trimethyl-1,4,7-triazacyclononane)manganese(IV)]bishexafluorophosphate monohydrate. The product is free from ligand salt (measurement limit <0.1% by weight) and manganese dioxide (measurement limit <0.1% by weight).

EXAMPLE 2

39.6 g of manganese dichloride 4-hydrate (0.2 mol) are introduced as initial charge in 110 g of water in a 1 liter flask and admixed with 34.3 g of 1,4,7-trimethyl-1,4,7-triazacyclononane (0.2 mol). The solution is cooled and admixed with a mixture of 60.3 g (0.301 mol) of 20% strength by weight sodium hydroxide solution and 226.7 g (0.2 mol) of 3% strength by weight hydrogen peroxide solution at 10 to 15° C. When the addition is complete, the reaction mixture (pH>12.5) is adjusted to a pH of 6 with 12.1 g of 50% strength by weight sulfuric acid. The solids (manganese oxides/hydroxides) of the reaction mixture are filtered off with suction and the resulting filtrate is admixed, at a pH of 6, with a solution of 34.9 g (0.214 mol) of ammonium hexafluorophosphate in 30 g of water, and then is after-stirred for 1 hour. The solid produced in the reaction mixture is filtered off with suction and washed twice with 70 g of ice-water in each case. Drying in a vacuum drying cabinet at 80° C. gives 67 g (83% yield) of orange-red tri-μ-oxobis[(1,4,7-trimethyl-1,4,7-triazacyclononane)manganese(IV)]bishexafluorophosphate monohydrate as at least 99% solid (according to HPLC). No ligand salt and manganese dioxide (measurement limit <0.1% by weight) can be detected in the product.

EXAMPLE 3

39.6 g of manganese dichloride 4-hydrate (0.2 mol) are introduced as initial charge in 110 g of water in a 1 liter flask and admixed with 34.3 g of 1,4,7-trimethyl-1,4,7-triazacyclononane (0.2 mol). After cooling to 5° C., a mixture of 60.3 g (0.301 mol) of 20% strength by weight sodium hydroxide solution and 226.7 g (0.2 mol) of 3% strength by weight hydrogen peroxide solution is added with temperature control. When the addition is complete, after-stirring is carried out for 5 minutes and the reaction mixture (pH>12.5) is adjusted to a pH of 6 with 12.1 g of 50% strength by weight sulfuric acid. The dark precipitates (manganese oxides/hydroxides) are filtered off with suction and the resulting filtrate is admixed, at a pH of 6, with an 80° C.-hot solution of 39.4 g (0.214 mol) of potassium hexafluorophosphate in 75 g of water. The solid produced in the reaction mixture is filtered off with suction and is washed twice with 70 g of ice-water in each case. Drying in a vacuum drying cabinet at 80° C. gives 67 g (83% yield) of tri-μ-oxobis[(1,4,7-trimethyl-1,4,7-triazacyclononane)manganese(IV)]bishexafluorophosphate monohydrate as at least 99% strength solid (according to HPLC). No ligand salt and manganese dioxide (measurement limit <0.1% by weight) can be detected in the product.

EXAMPLE 4

Synthesis of Mn/Fe complex $[Mn^{(IV)}Fe^{(III)}(\mu\text{-}O)_3(1,4,7\text{-}Me_3\text{-}TACN)_2]2PF_6 \cdot H_2O$ 19.8 g of manganese dichloride 4-hydrate (0.1 mol) and 19.9 g of iron(II) chloride (0.1 mol) are introduced as initial charge in 110 g of water in a 1 liter flask and admixed with 34.2 g of 1,4,7-trimethyl-1,4,7-triazacyclononane (0.2 mol). After cooling to 5° C., a mixture of 60.3 g (0.301 mol) of 20% strength by weight sodium hydroxide solution and 226.7 g (0.2 mol) of 3% strength by weight hydrogen peroxide solution is added with temperature control. When the addition is complete, after-stirring is carried out for 5 minutes and the reaction mixture (pH>12.5) is adjusted to a pH of 8.0 with 12.1 g of 50% strength by weight sulfuric acid.

The dark precipitates (manganese oxides/hydroxides) are filtered off with suction and the resulting filtrate is admixed at a pH of 8 with a 70° C.-hot solution of 39.4 g (0.214 mol) of potassium hexafluorophosphate in 75 g of water. The solid produced in the reaction mixture is filtered off with suction and washed twice with 70 g of ice-water in each case. Drying in a vacuum drying cabinet at 80° C. gives 48.3 g of Mn/Fe complex $[Mn^{(IV)}Fe^{(III)}(\mu\text{-}O)_3(1,4,7\text{-}Me_3\text{-}TACN)_2]2PF_6 \cdot H_2O$ as red-brown solid. A further 11.2 g of the complex separate off from the mother liquor. Total yield: 59.5 g. No ligand salt and manganese dioxide (measurement limit <0.1% by weight) can be detected in the product.

EXAMPLE 5

Synthesis of $[Mn^{(IV)}Mn^{(III)}(\mu\text{-}O)_3(4,7\text{-}Me_4\text{-}DTNE)]2PF_6 \cdot H_2O$ 8.5 g of 1,2-bis(4,7-dimethyl-1,4,7-triazacyclon-1-yl)ethane (Me$_4$-DTNE) (25 mmol) are reacted as per Example 3 with 4.95 g (25 mmol) of manganese dichloride 4-hydrate and oxidized at pH 12 to the $Mn^{(III)}/Mn^{(IV)}$ compound. After reducing the pH to 7.5 and separating off the manganese oxides, a hot solution of 4.6 g of KPF$_6$ in water is added at a pH of 7.5. After work-up, 12.7 g of greenish crystals of $[Mn^{(IV)}Mn^{(III)}(\mu\text{-}O)_3 (4,7\text{-}Me_4\text{-}DTNE)]2 PF_6 \cdot H_2O$ are isolated. No ligand salt and manganese dioxide (measurement limit <0.1% by weight) can be detected in the product.

The invention claimed is:
1. A method for producing a manganese complex compound of the formula (1)

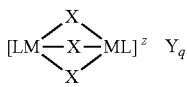

in which

M is selected from the group consisting of manganese in oxidation state III or IV and iron in oxidation state III or IV, where at least one M is a manganese in oxidation state III or IV, X independently of the others is a coordinating or bridging species, selected from the group consisting of $H_2O$, $O_2^{2-}$, $O_2^-$, $O^{2-}$, $OH^-$, $HO_2^-$, $SH^-$, $S^{2-}$, $SO$, $Cl^-$, $N^{3-}$, $SCN^-$, $N_3^-$, $RCOO^-$, $NH_2^-$ and $NR_3$, where R is a radical selected from the group consisting of H, alkyl and aryl, L is 1,4,7-trimethyl-1,4,7-triazacyclononane, z is an integer from −4 to +4, Y is a mono- or multivalent countering selected from the group consisting of hexafluorophosphate, perchlorate and tetraphenylborate, which leads to the charge neutrality of the complex, and q is an integer from 1 to 4, wherein the process comprises the following steps:

a) reacting at least one divalent metal salt, wherein the at least one divalent metal salt is selected from divalent manganese and iron salts and at least one divalent metal salt is a divalent manganese salt, with the ligand L in water as solvent forming a coordination compound of the at least one divalent metal salt and the ligand L, b) oxidizing the coordination compound from step a) with an oxidizing agent, where at the same time a pH from 11 to 14 is maintained, for converting the metal M from the divalent state to the tri- and/or tetravalent state, c) reducing the pH of the reaction mixture of step b) to a pH from 4 to 9, and separating off any metal oxides or hydroxides of the metal M formed and d) adding a salt of the formula $Me_zY_q$, in which Me is an alkali metal ion, an ammonium ion or an alkanolammonium ion, and Y, z and q are defined above, at a pH from 4 to 9 and where the counterion salt $Me_zY_q$ is only introduced into the reaction mixture and reacted after the oxidation step and the removal of the metal oxides and metal hydroxides formed, wherein the at least one divalent metal salt and the ligand compound during the reaction in step a) are present together in an amount of at least 15 parts by weight per 100 parts by weight of water.

2. The method as claimed in claim 1, further comprising precipitating and isolating the manganese complex compound of the formula (1) from the reaction mixture.

3. The method as claimed in claim 1, wherein M in the formula (1) is manganese in oxidation state III or IV and the at least one divalent metal salt from step a) is at least one divalent manganese salt.

4. The method as claimed in claim 1, wherein the at least one divalent metal salt and the ligand compound during the reaction in step a) are present together in an amount of 15 to 55 parts by weight per 100 parts by weight of water.

5. The method as claimed in claim 4, wherein the at least one divalent metal salt and the ligand compound during the reaction in step a) are present together in an amount of 20 to 50 parts by weight per 100 parts by weight of water.

6. The method as claimed in claim 1, wherein the oxidizing agent is selected from the group air, pure oxygen, hydrogen peroxide, alkali metal peroxide and alkali metal permanganate.

7. The method as claimed in claim 1, wherein the counterion Y is hexafluorophosphate.

8. A method for producing a manganese complex compound of the formula (1)

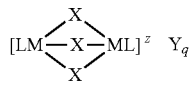

in which

M is selected from the group consisting of manganese in oxidation state III or IV and iron in oxidation state III or IV, where at least one M is a manganese in oxidation state III or IV, X independently of the others is a coordinating or bridging species, selected from the group consisting of $H_2O$, $O_2^{2-}$, $O_2^-$, $O^{2-}$, $OH^-$, $HO_2^-$, $SH^-$, $S^{2-}$, $SO$, $Cl^-$, $N^{3-}$, $SCN^-$, $N_3^-$, $RCOO^-$, $NH_2^-$ and $NR_3$, where R is a radical selected from the group consisting of H, alkyl and aryl, L is 1,4,7-trimethyl-1,4,7-triazacyclononane, z is an integer from −4 to +4, Y is a mono- or multivalent counterion selected from the group consisting of hexafluorophosphate, perchlorate and tetraphenylborate, which leads to the charge neutrality of the complex, and q is an integer from 1 to 4, wherein the process comprises the following steps:

a) reacting at least one divalent metal salt, wherein the at least one divalent metal salt is selected from divalent manganese and iron salts and at least one divalent metal salt is a divalent manganese salt, with the ligand L in water as solvent forming a coordination compound of the at least one divalent metal salt and the ligand L, b) oxidizing the coordination compound from step a) with an oxidizing agent, where at the same time a pH from 11 to 14 is maintained, for converting the metal M from the divalent state to the tri- and/or tetravalent state, c) reducing the pH of the reaction mixture of step b) to a pH from 4 to 9, and separating off any metal oxides or hydroxides of the metal M formed and d) adding a salt of the formula $Me_zY_q$, in which Me is an alkali metal ion, an ammonium ion or an alkanolammonium ion, and Y, z and q are defined above, at a pH from 4 to 9 and where the counterion salt $Me_zY_q$ is only introduced into the reaction mixture and reacted after the oxidation step and the removal of the metal oxides and metal hydroxides formed, wherein tri-μ-oxobis[(1,4,7-trimethyl-1,4,7-triazacyclononane)manganese(IV)]- bishexafluorophosphate monohydrate is produced.

9. The method as claimed in claim 1, wherein the crystalline precipitated manganese complex compound of the formula (1) in a further step e), is isolated by filtration or centrifugation.

10. The method as claimed in claim 1, wherein the oxidizing agent is selected from the group air, pure oxygen, hydrogen peroxide, alkali metal peroxide and alkali metal permanganate in combination with an alkali metal hydroxide.

11. The method as claimed in claim 8, further comprising precipitating and isolating the manganese complex compound of the formula (1) from the reaction mixture.

12. The method as claimed in claim 8, wherein M in the formula (1) is manganese in oxidation state III or IV and the at least one divalent metal salt from step a) is at least one divalent manganese salt.

13. The method as claimed in claim 8, wherein the at least one divalent metal salt and the ligand compound during the reaction in step a) are present together in an amount of at least 15 parts by weight per 100 parts by weight of water.

14. The method as claimed in claim 13, wherein the at least one divalent metal salt and the ligand compound during the reaction in step a) are present together in an amount of 15 to 55 parts by weight per 100 parts by weight of water.

15. The method as claimed in claim 14, wherein the at least one divalent metal salt and the ligand compound during the reaction in step a) are present together in an amount of 20 to 50 parts by weight per 100 parts by weight of water.

16. The method as claimed in claim 8, wherein the oxidizing agent is selected from the group air, pure oxygen, hydrogen peroxide, alkali metal peroxide and alkali metal permanganate.

17. The method as claimed in claim 8, wherein the counterion Y is hexafluorophosphate.

18. The method as claimed in claim 8, wherein the crystalline precipitated manganese complex compound of the formula (1) in a further step e), is isolated by filtration or centrifugation.

19. The method as claimed in claim 8, wherein the oxidizing agent is selected from the group air, pure oxygen, hydrogen peroxide, alkali metal peroxide and alkali metal permanganate in combination with an alkali metal hydroxide.

* * * * *